(12) United States Patent
Dandala et al.

(10) Patent No.: US 8,212,034 B2
(45) Date of Patent: Jul. 3, 2012

(54) PROCESS FOR PREPARING ROSUVASTATIN CALCIUM

(75) Inventors: Ramesh Dandala, Hyderabad (IN); Sambhu Prasad Sarma Mallela, Hyderabad (IN); Sukumar Nandi, Hyderabad (IN); Gangadhar Bhima Shankar Nangi, Hyderabad (IN); Sunil Kumar Buridipadu, Hyderabad (IN); Sivakumaran Meenakshisunderam, Hyderabad (IN)

(73) Assignee: Aurobindo Pharma Ltd., Hyderabad (IN)

( * ) Notice: Subject to any disclaimer, the term of this patent is extended or adjusted under 35 U.S.C. 154(b) by 438 days.

(21) Appl. No.: 12/448,270

(22) PCT Filed: Dec. 11, 2007

(86) PCT No.: PCT/IB2007/003936
§ 371 (c)(1),
(2), (4) Date: Jun. 12, 2009

(87) PCT Pub. No.: WO2008/072078
PCT Pub. Date: Jun. 19, 2008

(65) Prior Publication Data
US 2010/0029940 A1    Feb. 4, 2010

(30) Foreign Application Priority Data
Dec. 13, 2006    (IN) ............................ 2308/CHE/2006

(51) Int. Cl.
C07D 239/42    (2006.01)
(52) U.S. Cl. ...................................................... 544/332
(58) Field of Classification Search .................... 544/332
See application file for complete search history.

(56) References Cited

U.S. PATENT DOCUMENTS

| | | | |
|---|---|---|---|
| 5,260,440 A | 11/1993 | Hirai | |
| RE37,314 E | 8/2001 | Hirai et al. | |
| 7,161,004 B2 | 1/2007 | Gudipati | |
| 7,179,916 B2 | 2/2007 | Niddam-Hildesheim | |
| 2005/0222415 A1 | 10/2005 | Kumar | |
| 2008/0091014 A1 | 4/2008 | Huang | |

FOREIGN PATENT DOCUMENTS

| | | |
|---|---|---|
| CN | 1763015 A | 10/2004 |
| CZ | 298330 B6 | 7/2004 |
| WO | WO 2000/049014 | 8/2000 |
| WO | WO 2003/097614 | 11/2003 |
| WO | WO 2004/014872 | 2/2004 |
| WO | WO 2004/052867 | 6/2004 |
| WO | WO 2006/100689 | 9/2006 |
| WO | WO 2006/106526 | 10/2006 |
| WO | WO 2006/128954 A1 | 12/2006 |
| WO | WO 2007/007119 A1 | 1/2007 |
| WO | WO 2007/074391 A2 | 7/2007 |

OTHER PUBLICATIONS

Hideg et al., CASREACT Abstract 94:121217 (1980), 2 pages.*

* cited by examiner

Primary Examiner — Deepak Rao
(74) Attorney, Agent, or Firm — Jay R. Akhave

(57) ABSTRACT

The present invention relates to an improved process for preparing (2E)-3-[4-(4-fluorophenyl)-6-iso-propyl-2-(N-methyl-N-methylsulfonylamino)pyrimidin-5-yl]-propenal of Formula I which is an intermediate useful in the preparation of bis[(E)-7-[4-(4-fluorophenyl)-6-isopropyl-2-[methyl (methylsulfonyl)amino]pyrimidin-5-yl](3R,5S)-3,5-dihydroxyhept-6-enoicacid]calcium salt of Formula II.

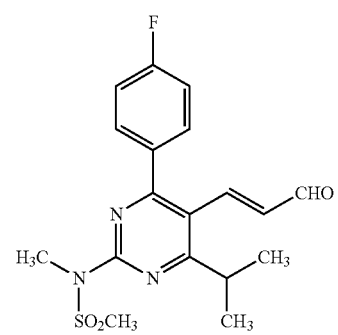

(I)

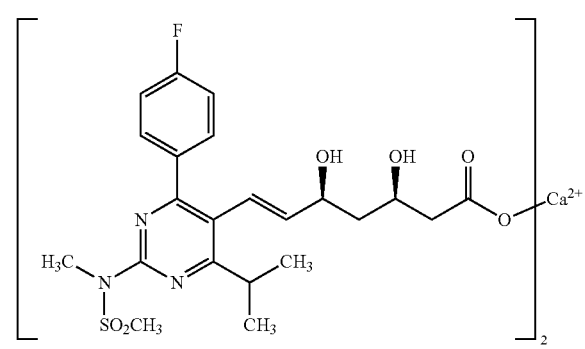

(II)

9 Claims, No Drawings

PROCESS FOR PREPARING ROSUVASTATIN CALCIUM

This application is a 371 of PCT/IB2007/003936 filed Dec. 11, 2007.

FIELD OF THE INVENTION

The present invention relates to an improved process for preparing (2E)-3-[4-(4-fluorophenyl)-6-isopropyl-2-(N-methyl-N-methylsulfonylamino)pyrimidin-5-yl]-propenal of Formula I

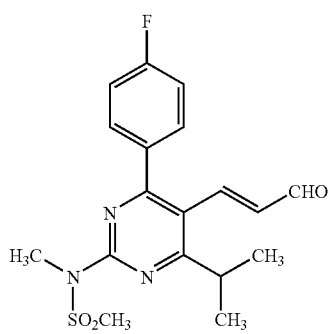

Formula I which is an intermediate useful in the preparation of bis[(E)-7-[4-(4-fluorophenyl)-6-isopropyl-2-[methyl(methylsulfonyl)amino]pyrimidin-5-yl](3R,5S)-3,5-dihydroxyhept-6-enoicacid]calcium salt of Formula II

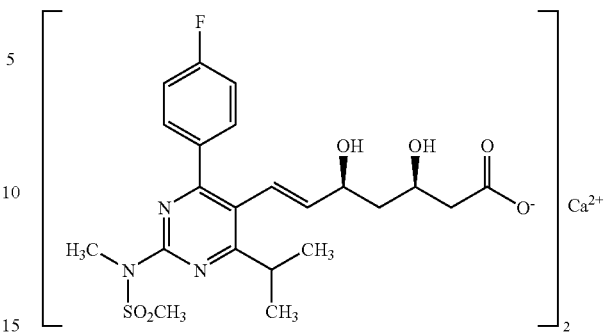

Formula II

BACKGROUND OF THE INVENTION

Rosuvastatin, which is an antihyperchlolesterolemic drug, is chemically known as (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium (2:1) salt of Formula I.

Rosuvastatin was for the first time disclosed in U.S. Pat. No. 5,260,440. Rosuvastatin is being marketed under the proprietary name CRESTOR, as an oral tablet, for the treatment of hypercholesterolemia. In view of the importance of Rosuvastatin as a lipid-lowering agent, several synthetic methods have been reported in the literature to prepare Rosuvastatin, some of which are summarized below:

U.S. Pat. No. 5,260,440 discloses a process for preparing Rosuvastatin in examples. The process is as shown below:

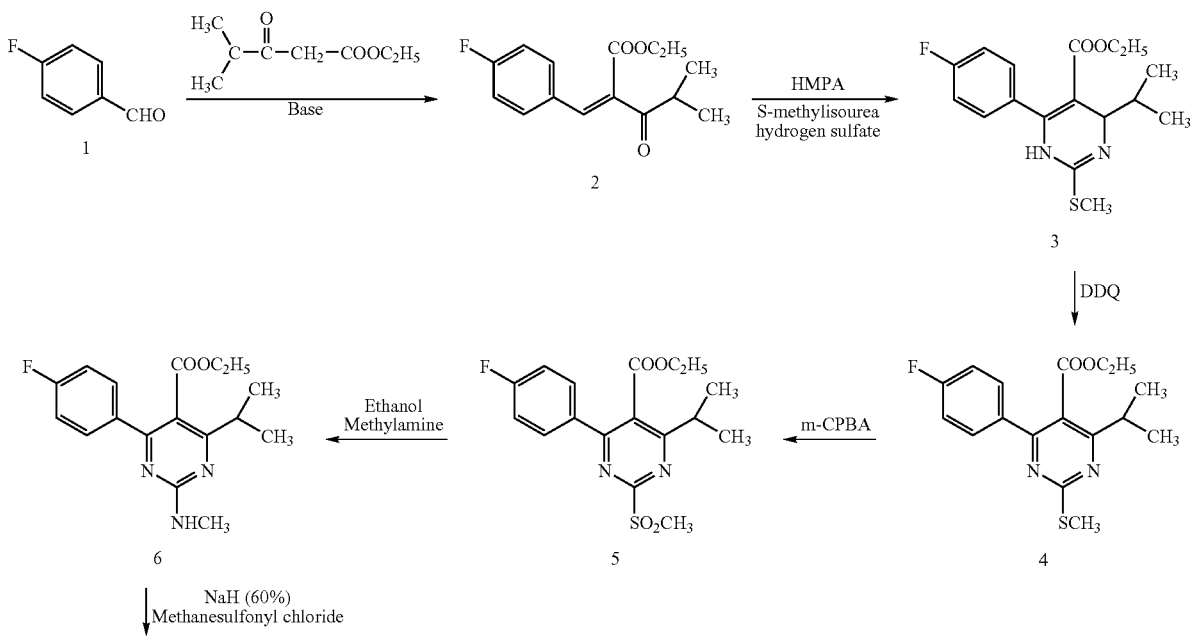

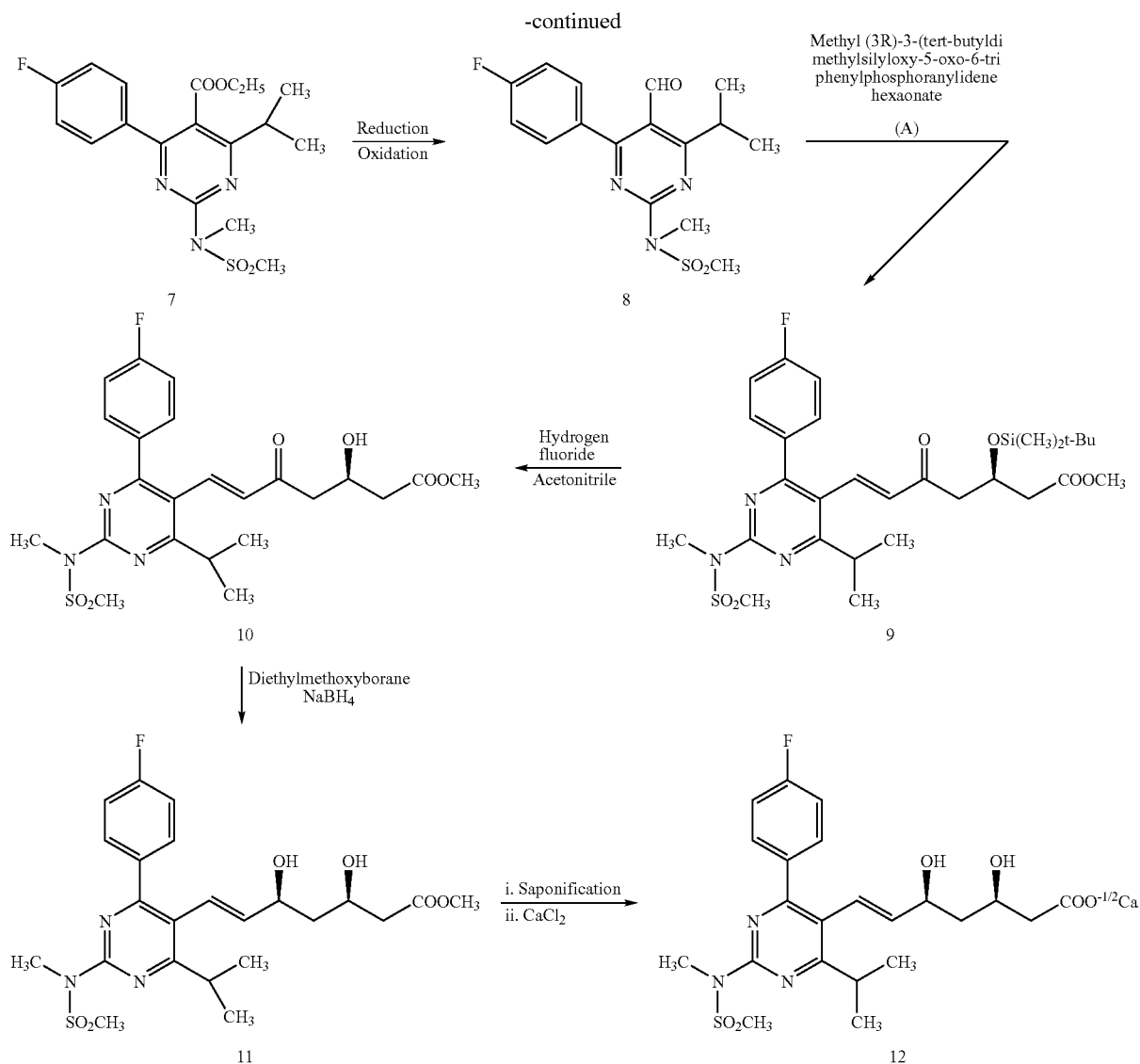

The difficulties in the above process are that the intermediate (A) is not obtained in pure form readily and its purification is tedious and overall yield is extremely low. Even when intermediate (A) is obtained in pure form, further condensation with intermediate (X) to form Rosuvastin, does not result in Rosuvastatin of right quality as the product contains unacceptable quantity of impurity levels.

WO 03/097614 describes a modified procedure for the preparation of the starting material 4-(4-fluorophenyl)-6-isopropyl-2-[methyl(methylsulfonyl)amino]pyrimidin-5-carbaxldehyde and further conversion to Rosuvastatin by condensing with methyl (3R)-3-[(tert-butyldimethylsilyl)oxy]-5-oxo-6-triphenylphosphoranylidene hexanoate. The condensed product was deprotected using methanesulfonic acid and subsequently converted to Rosuvastatin calcium (2:1) salt.

WO 2004/052867 describes a process to prepare Rosuvastatin by condensing 1-cyano(2S)-2-[(tert-butyldimethylsilyl)oxy]-4-oxo-5-triphenylphosphoran-ylidene pentane with 4-(4-fluorophenyl)-6-isopropyl-2-[methyl(methylsulfonyl)amino]pyrimidin-5-carbaldehyde and subsequent deprotection of silyl group, followed by reduction and hydrolysis.

WO 2000/049014 discloses a novel chemical process for the manufacture of tert-butyl (E)-(6-{2-[4-(4-fluorophenyl)-6-isopropyl-2-methyl(methylsulfonyl)amino]pyrimidin-5-yl]vinyl}-(4R,6S)-2,2-dimethyl[1,3]dioxan-4-yl)acetate which comprises reaction of diphenyl {4-(4-fluorophenyl)-6-isopropyl-2-[methyl(methylsulfonyl)amino]pyrimidin-5-yl-methyl}phosphineoxide with tert-butyl 2-[(4R,6S)-6-formyl-2,2-dimethyl-1,3-dioxan-4-yl]acetate and its further conversion to Rosuvastatin.

WO 2004/014872 describes a process for the manufacture of Rosuvastatin calcium (2:1) salt which comprises mixing a solution of calcium chloride with a solution of water soluble salt of (E)7-[4-(4-fluorophenyl)-6-isopropyl-2-[methyl(methylsulfonyl)amino]pyrimidin-5-yl](3R,5S)-3,5-dihydroxy-hept-6-enoic acid. This process for the preparation of Rosuvastatin employs the use of phosphorane side chain, the preparation of side chain requires eight synthetic steps and involves expensive reagents. The process is both uneconomical and time consuming, hence not appropriate for commercial scale operation.

WO 2006/100689 A1 discloses a process for preparation of Rosuvastatin as shown below:
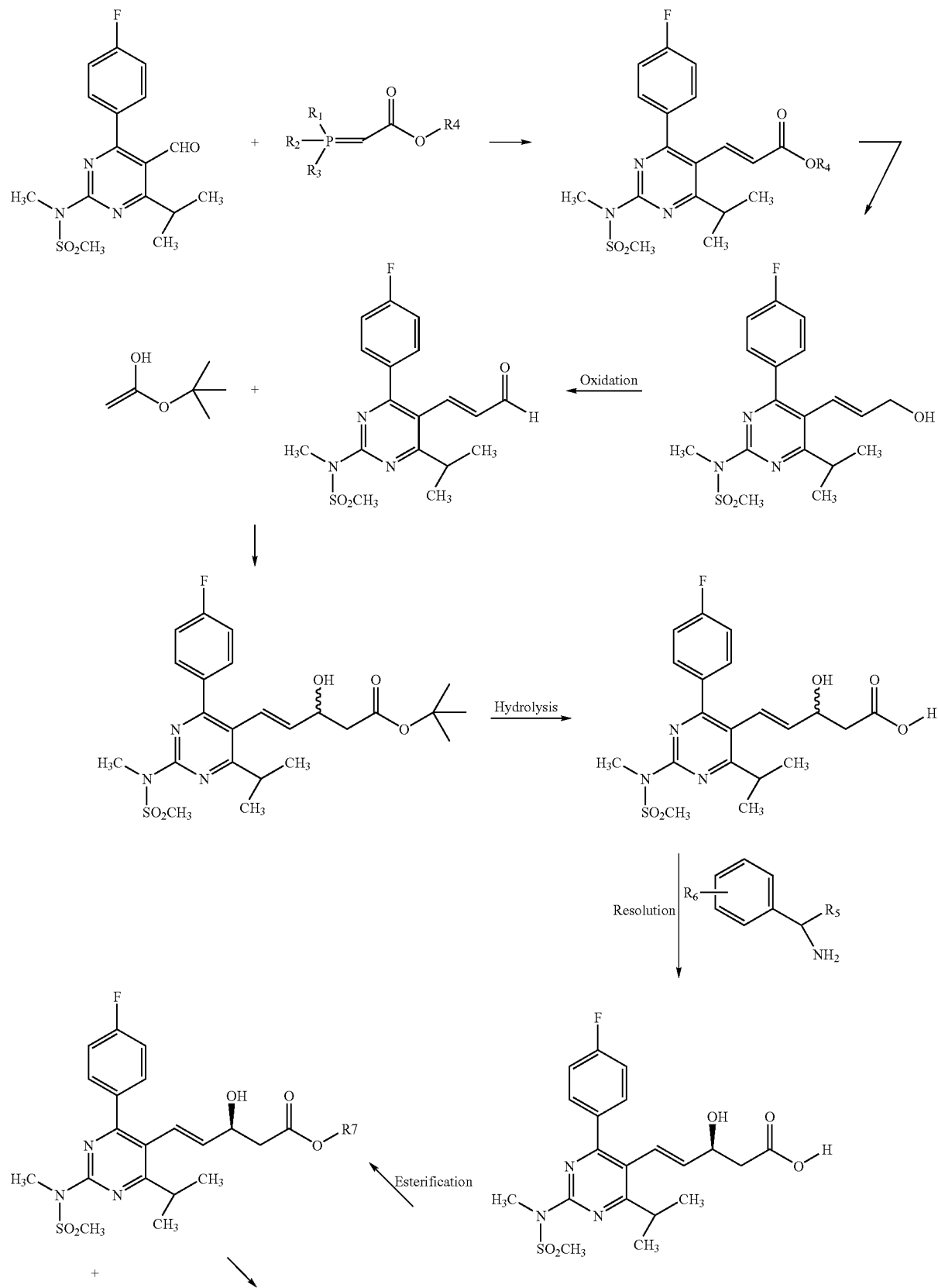

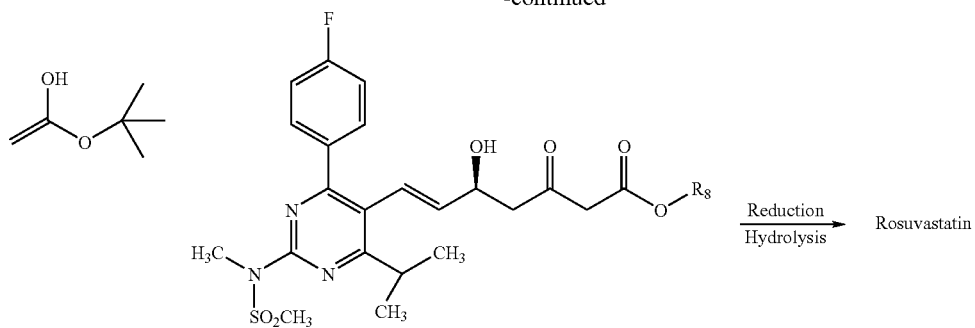

In the above scheme $R_1$, $R_2$, $R_3$ represent substituted or unsubstituted phenyl and $R_4$ represents an aliphatic residue selected from $C_1$-$C_4$ alkyl, $R_5$ represents $C_1$-$C_4$ alkyl which is optionally substituted by hydroxyl, $R_6$ represents hydrogen, halogen, $C_1$-$C_4$ alkyl or $C_1$-$C_4$ alkoxy, $R_7$ represents aliphatic residue, $R_8$ represents $C_1$-$C_4$ alkyl WO 2006/106526 A1 describes the preparation of Rosuvastatin as shown below:

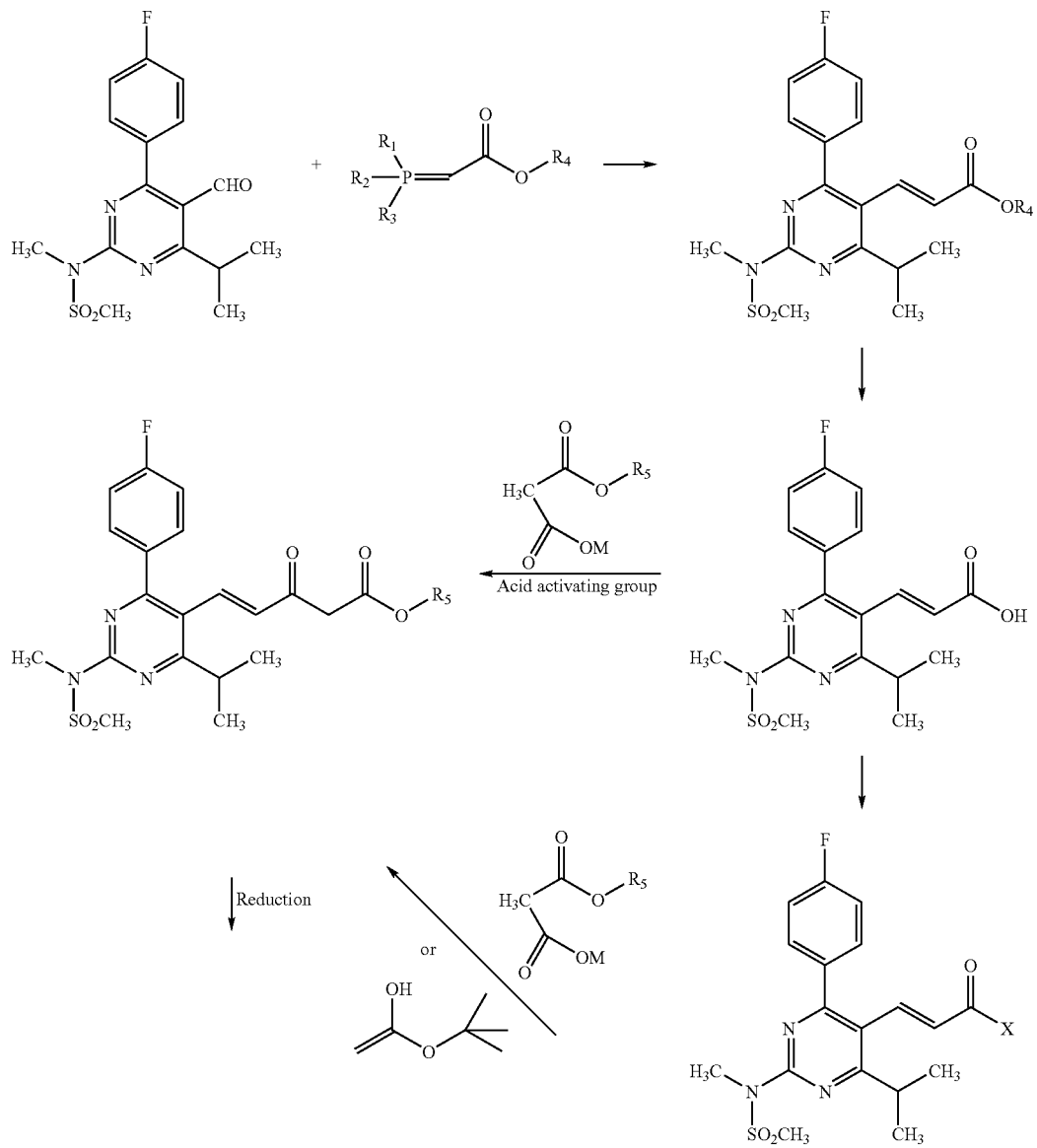

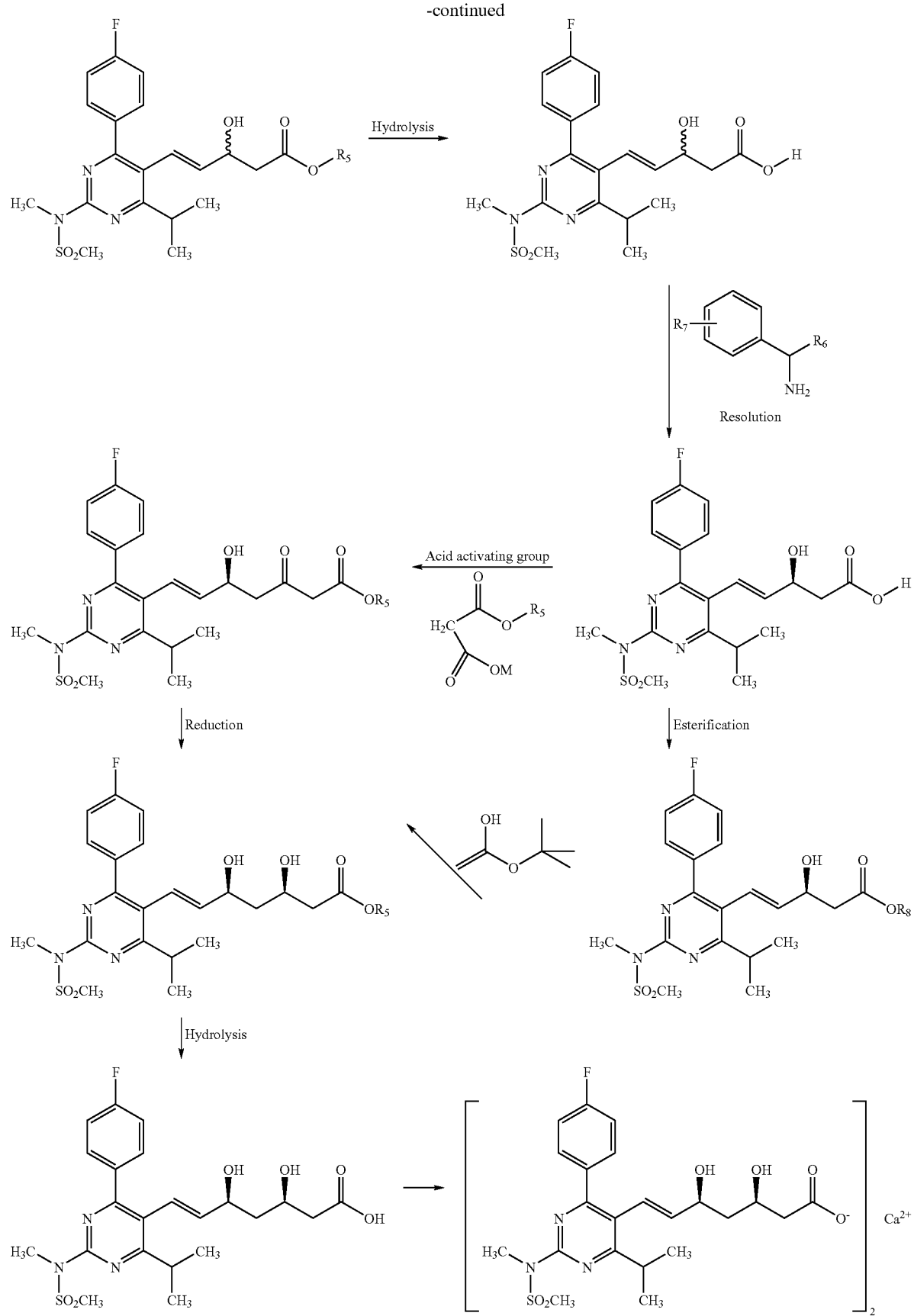

In the above mentioned scheme $R_1$, $R_2$, $R_3$ are substituted or unsubstituted phenyl and $R_4$ is an aliphatic residue selected from $C_1$-$C_4$ alkyl, $R_5$ represents $C_1$-$C_4$ alkyl, M is an alkali metal salt, X represents a halogen, $R_6$ represents $C_1$-$C_4$ alkyl which is optionally substituted by hydroxyl, $R_7$ represents hydrogen, halogen, $C_1$-$C_4$ alkyl or $C_1$-$C_4$ alkoxy, $R_8$ is an aliphatic residue selected from $C_1$-$C_4$ alkyl.

We have now found an improved process to prepare (2E)-3-[4-(4-fluorophenyl)-6-isopropyl-2-(N-methyl-N-methylsulfonylamino)pyrimidin-5-yl]-propenal of Formula I and subsequently converting the compound of Formula I to Rosuvastatin.

OBJECTIVE

The main objective of the present invention is to provide an improved process for preparing (2E)-3-[4-(4-fluorophenyl)-6-isopropyl-2-(N-methyl-N-methylsulfonylamino)pyrimidin-5-yl]-propenal which is useful intermediate in the preparation of Rosuvastatin.

Yet another objective of the present invention is to provide an improved process for preparing (2E)-3-[4-(4-fluorophenyl)-6-isopropyl-2-(N-methyl-N-methylsulfonylamino)pyrimidin-5-yl]-propenal, which is simple, industrially applicable and economically viable.

Another objective of the present invention is to provide a process for a novel intermediate that is used in the preparation of Rosuvastatin calcium.

SUMMARY OF THE INVENTION

The present invention relates to an improved process for preparing (2E)-3-[4-(4-fluorophenyl)-6-isopropyl-2-(N-methyl-N-methylsulfonylamino)pyrimidin-5-yl]-propenal of Formula I, Formula I

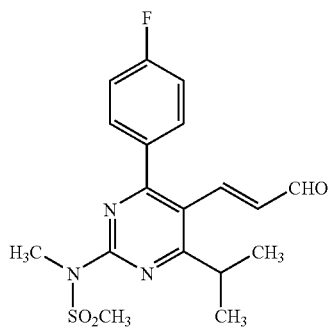

which comprises:
a) reacting 4-(4-fluorophenyl)-6-isopropyl-2-(N-methyl-N-methylsulfonylamino)pyrimidin-5-yl]-carboxaldehyde of Formula III, Formula III

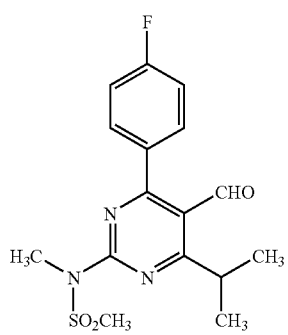

with a compound of Formula IV a or Formula IV b in an inert organic solvent

Formula IV a

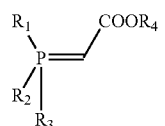

Formula IV b

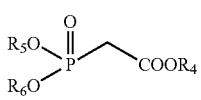

wherein $R_1$, $R_2$, $R_3$, represents phenyl, substituted phenyl, $R_4$ represents an aliphatic residue selected from $C_{1-4}$ alkyl, $R_5$ and $R_6$ represent $C_{1-4}$ alkyl, aralkyl, phenyl and substituted phenyl to obtain a compound of Formula V, Formula V

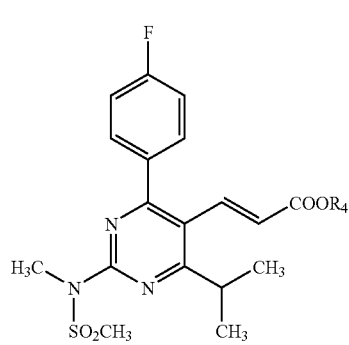

wherein $R_4$ is as defined above,
b) converting the compound of Formula V with an aqueous base in a water miscible solvent to give a compound of Formula VI, Formula VI

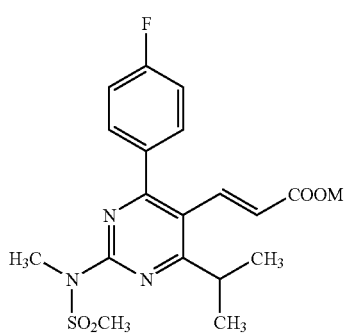

wherein M represents hydrogen or alkali metal,
c) treating the compound of Formula VI with a compound of Formula VII, Formula VII

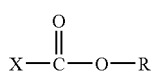

X represents halogen and R represents $C_{1-4}$ alkyl in the presence of an organic base in an inert solvent to give a compound of Formula VIII, Formula VIII

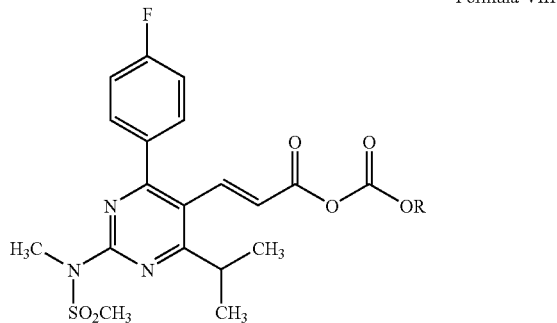

wherein R is as defined above, d) reducing the compound of Formula VIII to give a (2E)-3-[4-(4-fluorophenyl)-6-isopropyl-2-(N-methyl-N-methylsulfonylamino)pyrimidin-5-yl]propen-1-ol of Formula IX, Formula IX

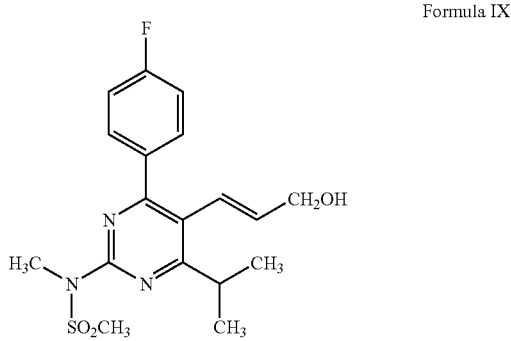

e) oxidizing the compound of Formula IX to give 3-[4-(4-fluorophenyl)-6-isopropyl-2-(N-methyl-N-methylsulfonylamino)pyrimidin-5-yl]-propenal of Formula I.

In another embodiment of the present invention, the (2E)-3-[4-(4-fluorophenyl)-6-isopropyl-2-(N-methyl-N-methylsulfonylamino)pyrimidin-5-yl]-propenal of Formula I is converted to Rosuvastatin and its pharmaceutically acceptable salts thereof.

DETAILED DESCRIPTION OF THE INVENTION

The main objective of the present invention is to provide a new improved process for the preparation of Rosuvastatin in high yield and high purity.

Another objective of the present invention is to develop a new process for the preparation of compound of Formula I so as to facilitate the preparation of Rosuvastatin in high yield and high purity.

The compound of Formula III is reacted with phosphorane of Formula IV a or phosphonate of Formula IV b in an inert organic solvent like acetonitrile, tetrahydrofuran or alcoholic solvents like isopropyl alcohol, methanol, ethanol or methyl tert-butyl ether, toluene, halogenated hydrocarbons like methylene chloride or ethylene dichloride, optionally in the presence of a base at temperature in the range of 0-100° C., preferably between 20-80° C. The preferred solvent is isopropanol. The condensation reaction of compound of Formula III with compound of Formula IV a or IV b results in the formation of compound of Formula V.

The compound of Formula V is converted to compound of Formula VI in the presence of aqueous base in water miscible solvent. The aqueous base can be selected from sodium hydroxide, potassium hydroxide, lithium hydroxide, barium hydroxide etc more preferably sodium hydroxide. The water miscible solvent is selected from ethanol, methanol, tetrahydrofuran, isopropyl alcohol etc. The reaction is conducted at a temperature ranging from 0-80° C., preferably at 0-30° C. The hydrolysis reaction yields the compound of Formula VI that is isolated as an alkali metal salt.

The compound of Formula VI is further converted to its mixed anhydride by treating the compound of Formula VI with a compound of Formula VII in the presence of an organic base like trialkylamines in an inert solvent. The compound of Formula VII is selected from methyl chloroformate, ethyl chloroformate, 2,2,2-trichloroethylchloroformate etc. more preferably methyl chloroformate.

The inert solvent is selected from methylene chloride, ethylene dichloride, toluene, hexane etc more preferably methylene chloride. This reaction is conducted at a temperature ranging from −50° C. to 50° C., more preferably at 0-10° C. to obtain compound of Formula VIII. The compound of Formula VIII can be optionally crystallized using suitable organic solvent like hexane, heptane, ethyl acetate, toluene or a mixture thereof.

The compound of Formula VIII is reduced to compound of Formula IX with reducing agents like lithium aluminium hydride, diisobutyl aluminium hydride, sodium borohydride, vitride etc. The reduction is performed in suitable inert organic solvent like tetrahydrofuran, toluene, methyl tert-butyl ether, isopropyl ether etc more preferably tetrahydrofuran. The reduction step is performed in the temperature ranging from −80° C. to 80° C., more preferably −80° C. to −15° C. to give compound of Formula IX.

The compound of Formula IX is further oxidized to compound of Formula I using Pyridinium dichromate, pyridinium chloroformate, 1,2,2,6,6-tetramethyl-1-piperidinyloxy catalyzed sodium hypochlorite, tetrapropyl ammoniumperruthenate with N-methylmorpholine N-oxide, swern oxidation, manganese dioxide etc, more preferably manganese dioxide in an inert organic solvent like methylene chloride, ethylene dichloride, toluene, hexane, heptane etc, more preferably toluene.

Finally the compound of Formula I is converted to Rosuvastatin by the known methods reported in literature.

The invention is illustrated with the following examples, which are provided by way of illustration only and should not be construed to limit the scope of the invention.

EXAMPLE 1

Preparation of 3-[4-(4-fluorophenyl)-6-isopropyl-2-(N-methyl-N-methylsulfonylamino)pyrimidin-5-yl] (2E)-propenoic Acid A suspension of methyl 3-[4-(4-fluorophenyl)-6-isopropyl-2-(N-methyl-N-methylsulfonylamino)pyrimidin-5-yl] (2E)-propenoate (10 g) in ethanol (200 ml) was treated with aqueous sodium hydroxide solution (0.1N, 246 ml) at 0-5° C. The reaction mixture was stirred at 25-30° C. for 12 h for completion of hydrolysis and ethanol was evaporated under reduced pressure. The resulting mass was acidified and extracted with methylene chloride (2×100 ml). The organic layer was washed with water, dried and concentrated to give the title product (Yield 9.4 g).

$^1$H NMR (300 MHz) in DMSO-$d_6$ δ (ppm): 1.32 [d, J=9 Hz, 6H], 3.35-3.46 [m, 1H], 3.60 (s, 3H,), 3.62 (s, 3H), 5.8 (d, 1H, J=15 Hz, H), 7.17 (m, 2H), 7.59 (m, 2H), 7.84 (d, 2H, J=15 Hz)

EXAMPLE 2

Preparation of 3-[4-(4-fluorophenyl)-6-isopropyl-2-(N-methyl-N-methylsulfonylamino)pyrimidin-5-yl](2E)-propenoyl Methyl Carbonate 3-[4-(4-Fluorophenyl)-6-isopropyl-2-(N-methyl-N-methylsulfonylamino)pyrimidin-5-yl](2E)-propenoic acid (5 g, 0.012 m) was dissolved in methylene chloride (25 ml) and triethylamine (1.54 g, 0.015 m) was added at 25° C. The mixture was cooled to 0° C. and methyl chloroformate (1.31 g, 0.013 m) was added to the reaction mass slowly over a period of 10 min keeping the temperature below 5° C. The reaction mixture was stirred at 0-5° C. for 30 min and water (25 ml) was added to it. The organic layer was separated and washed with aqueous sodium bicarbonate solution (5% w/v, 20 ml) followed by water (20 ml). Methylene chloride was distilled out under reduced pressure at 40-45° C. to obtain the product as an oily mass, which was crystallized from n-hexane to obtain while crystalline solid (Yield: 5.4 g, 98%).

$^1$H NMR (300 MHz in CDCl$_3$; δ(ppm): 1.32 [d, 6H, J=9 Hz), 3.35-3.42 [m, 1H), 3.52 (s, 3H), 3.6 (s, 3H), 3.94 (s, 3H), 5.87 (d, 1H, J=15 Hz, H), 7.15 (m, 2H), 7.59 (m, 2H), 7.91 (d, 2H, J=15 Hz).

EXAMPLE 3

Preparation of 3-[4-(4-fluorophenyl)-6-isopropyl-2-(N-methyl-N-methylsulfonylamino)pyrimidin-5-yl](2E)-propenol LiAlH$_4$ (0.5 g, 0.01 m) in tetrahydrofuran (50 ml) was cooled to −50° C. and a solution of 3-[4-(4-fluorophenyl)-6-isopropyl-2-(N-methyl-N-methylsulfonylamino)pyrimidin-5-yl](2E)-propenoyl methyl carbonate (5 g, 0.01 m) in tetrahydrofuran (15 ml) was added dropwise, over a period of 15 min, keeping the temperature below −45° C. The reaction mixture was stirred for 30 min at −45 to −50° C. and brought to room temperature. The reaction mixture was quenched by adding 1N hydrochloric acid (20 ml) and filtered through hyflo. The product was extracted using ethyl acetate (2×25 ml) and washed with water (25 ml). The organic layer was dried over sodium sulfate and evaporated to obtain the pure pyrimidine alcohol (Yield: 4.3 g, 98%).

EXAMPLE 4

Preparation of 3-[4-(4-fluorophenyl)-6-isopropyl-2-(N-methyl-N-methylsulfonylamino)pyrimidin-5-yl]-(2E)-propenol To a cold mixture of 3-[4-(4-fluorophenyl)-6-isopropyl-2-[methyl(methylsulfonyl)amino]-pyrimidin-5-yl]-(2E)-acrylic acid (5 ml) in THF (50 ml) methylchloroformate (1.5 ml) was added dropwise at 0-5° C. Reaction mixture was stirred at this temperature for 30 min and sodium borohydride (0.5 g) was added at 0-5° C. The reaction mixture was allowed to warm to room temperature and stirred at room temperature for 30 h. After completion of the reaction, mixture was poured on a cold HCl (100 ml) and extracted with ethyl acetate (50 ml). Organic phase was washed with aqueous sodium bicarbonate (2×50 ml), dried and evaporated to give crude product which was purified by column chromatography using ethyl acetate and hexanes (1:9) to give pure 3-[4-(4-fluorophenyl)-6-isopropyl-2-(N-methyl-N-methylsulfonylamino)pyrimidin-5-yl]-(2E)-propenol.

EXAMPLE 5

Preparation of 3-[4-(4-fluorophenyl)-6-isopropyl-2-(N-methyl-N-methylsulfonylamino)pyrimidin-5-yl]-(2E)-propenol To a solution of 3-[4-(4-fluorophenyl)-6-isopropyl-2-[methyl(methylsulfonyl)amine]-pyrimidin-5-yl]-(2E)-1-oxo-propenyl-methylcarbonate (0.5 g) in THF (50 ml) sodium borohydride (0.05 g) was added at 0-5° C. and the reaction mixture was allowed to warm to room temperature and stirred for 30 h. After the usual work-up, the reaction product was purified by column chromatography using hexanes and ethylacetate (9:1) to yield 0.4 g of 3-[4-(4-fluorophenyl)-6-isopropyl-2-(N-methyl-N-methylsulfonylamino)pyrimidin-5-yl]-(2E)-propenol.

EXAMPLE 6

Preparation of 3-[4-(4-fluorophenyl)-6-isopropyl-2-(N-methyl-N-methylsulfonylamino)pyrimidin-5-yl]-(2E)-propenal 3-[4-(4-Fluorophenyl)-6-isopropyl-2-(N-methyl-N-methylsulfonylamino)pyrimidin-5-yl](2E)-propen-1-ol-(5 g) was dissolved in toluene (50 ml) at 25° C. and manganese dioxide (20 g) was added to it. The reaction mixture was stirred for 5 h at 25° C. After completion of the reaction, reaction mixture was filtered through hyflo and toluene was evaporated under reduced pressure at 40° C. to obtain the product as a semi solid. The product was further crystallized from hexane-ethyl acetate (20 ml, 9:1 v/v) (Yield: 4.8 g).

We claim:
1. An improved process for preparing (2E)-3-[4-(4-fluorophenyl)-6-isopropyl-2-(N-methyl-N-methylsulfonylamino)pyrimidin-5-yl]-propenal of Formula I,

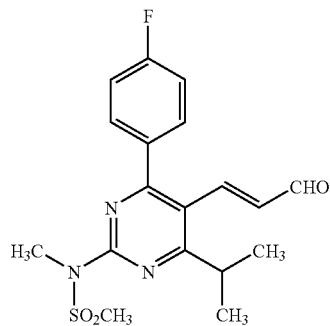

Formula I which comprises:
a) reacting 4-(4-fluorophenyl)-6-isopropyl-2-(N-methyl-N-methylsulfonylamino)pyrimidin-5-yl]-carboxaldehyde of Formula III,

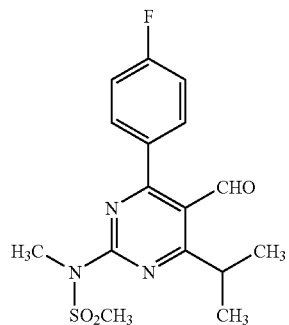

Formula III with a compound of Formula IV a or Formula IV b, in an inert organic solvent

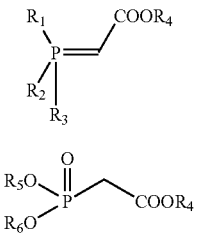
Formula IV a

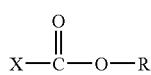
Formula IV b wherein $R_1$, $R_2$, $R_3$, represents phenyl, substituted phenyl, $R_4$ represents an aliphatic residue selected from $C_{1-4}$ alkyl, $R_5$ and $R_6$ represent $C_{1-4}$ alkyl, aralkyl, phenyl and substituted phenyl to obtain a compound of Formula V,

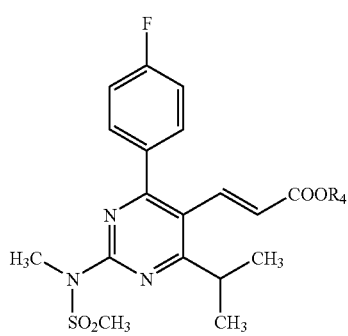
Formula V wherein $R_4$ is as defined above,
b) converting the compound of Formula V with an aqueous base in a water miscible solvent to give a compound of Formula VI,

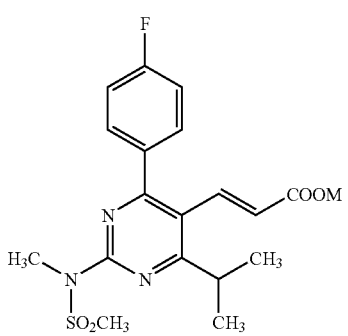
Formula VI wherein M represents hydrogen or alkali metal,
c) treating the compound of Formula VI with a compound of Formula VII, Formula VII $$X-\overset{O}{\underset{\|}{C}}-O-R$$

X represents halogen and R represents $C_{1-4}$ alkyl in the presence of an organic base in an inert solvent to give a compound of Formula VIII,

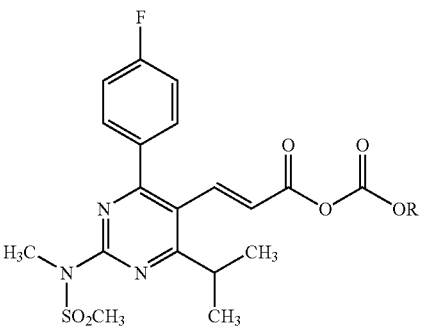
Formula VIII wherein R is as defined above,
d) reducing the compound of Formula VIII to give a (2E)-3-[4-(4-fluorophenyl)-6-isopropyl-2-(N-methyl-N-methylsulfonylamino)pyrimidin-5-yl]propen-1-ol of Formula IX, Formula IX e) oxidizing the compound of Formula IX to give 3-[4-(4-fluorophenyl)-6-isopropyl-2-(N-methyl-N-methylsulfonylamino)pyrimidin-5-yl]-propenal of Formula I.

2. The process according to claim 1, wherein 3-[4-(4-fluorophenyl)-6-isopropyl-2-(N-methyl-N-methylsulfonylamino)pyrimidin-5-yl]-propenal of Formula I is further converted to Rosuvastatin or its pharmaceutically acceptable salts.

3. The process according to claim 1, wherein the inert organic solvent used in step (a) is selected from acetonitrile, tetrahydrofuran, isopropyl alcohol, methanol, ethanol, methyl tert-butyl ether, toluene, methylene chloride and ethylene dichloride.

4. The process according to claim 1, wherein aqueous base used in step (b) is selected from sodium hydroxide, potassium hydroxide, lithium hydroxide and barium hydroxide.

5. The process according to claim 1, wherein the water miscible solvent is selected from ethanol, methanol, tetrahydrofuran and isopropyl alcohol.

6. The process according to claim 1, wherein the organic base is trialkylamine.

7. The process according to claim 1, wherein the inert solvent is selected from methylene chloride, ethylene dichloride, toluene and hexane.

8. The process according to claim 1, wherein the reducing agent used in step (d) is selected from lithium aluminium hydride, diisobutyl aluminium hydride, sodium borohydride and vitride.

9. The process according to claim 1, wherein the oxidizing agent used in step (e) is selected from pyridinium dichromate, pyridinium chloroformate, 1,2,2,6,6-tetramethyl-1-piperidinyloxy catalyzed sodium hypochlorite, tetrapropyl ammoniumperruthenate with N-methylmorpholine N-oxide and manganese dioxide.

* * * * *